United States Patent
Averikou et al.

(10) Patent No.: US 9,576,357 B2
(45) Date of Patent: Feb. 21, 2017

(54) ELIMINATING MOTION EFFECTS IN MEDICAL IMAGES CAUSED BY PHYSIOLOGICAL FUNCTION

(71) Applicants: KONINKLIJKE PHILIPS N.V., Eindhoven (NL); Michalakis Averikou, Eindhoven (NL); Damianos Christophides, Eindhoven (NL)

(72) Inventors: Michalakis Averikou, Eindhoven (NL); Damianos Christophides, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/760,736

(22) PCT Filed: Jan. 15, 2014

(86) PCT No.: PCT/IB2014/058293
§ 371 (c)(1),
(2) Date: Jul. 14, 2015

(87) PCT Pub. No.: WO2014/111860
PCT Pub. Date: Jul. 24, 2014

(65) Prior Publication Data
US 2015/0371379 A1    Dec. 24, 2015

Related U.S. Application Data

(60) Provisional application No. 61/753,898, filed on Jan. 17, 2013.

(51) Int. Cl.
*G06K 9/00* (2006.01)
*G06T 7/00* (2006.01)
(Continued)

(52) U.S. Cl.
CPC ............... *G06T 7/0012* (2013.01); *A61B 8/06* (2013.01); *A61B 8/481* (2013.01); *A61B 8/483* (2013.01);
(Continued)

(58) Field of Classification Search
CPC ....................................................... A61B 8/483
See application file for complete search history.

(56) References Cited

U.S. PATENT DOCUMENTS

| | | | |
|---|---|---|---|
| 5,577,505 | A | 11/1996 | Brock-Fisher et al. |
| 5,706,819 | A | 1/1998 | Hwang et al. |

(Continued)

FOREIGN PATENT DOCUMENTS

| | | |
|---|---|---|
| WO | 2005054898 A1 | 6/2005 |
| WO | 2005099579 A1 | 10/2005 |
| WO | 2006090309 A2 | 8/2006 |

OTHER PUBLICATIONS

"An Original Methodology for Quantitative Assessment of Perfusion in Small Animal Studies Using Contrast-Enhanced Ultrasound" Mule et al, 2007 Annual International Conference of the IEEE Engineering in Medicine and Biology Society, Lyon France, Aug. 22-26, 1007.

(Continued)

*Primary Examiner* — Oneal R Mistry (57) ABSTRACT

Ultrasonic imaging methods are described for eliminating the effects of physiological motion such as respiratory motion from image data of a sequence of images which is to be used for quantified analysis such as time-intensity curve computation. A bright reflector in the images of the loop which exhibits motional effects such as cyclical variation in brightness or position from image to image is identified and its variation used to identify cycles of motion. A phase or range of phases of the cycles is identified. Images acquired (Continued)

during the identified phase or phase range of the motion cycles during the loop are then used for quantified processing.

14 Claims, 8 Drawing Sheets

(51) Int. Cl.
 *A61B 8/06* (2006.01)
 *A61B 8/08* (2006.01)
 *G06T 7/20* (2006.01)
(52) U.S. Cl.
 CPC ........... *A61B 8/5223* (2013.01); *A61B 8/5276* (2013.01); *A61B 8/5284* (2013.01); *G06T 7/2033* (2013.01); *G06T 2207/10004* (2013.01); *G06T 2207/30096* (2013.01)

(56) References Cited

U.S. PATENT DOCUMENTS

| | | | |
|---|---|---|---|
| 5,833,613 | A | 11/1998 | Averkiou |
| 5,951,478 | A | 9/1999 | Hwang et al. |
| 6,692,438 | B2 | 2/2004 | Skyba et al. |
| 8,529,453 | B2 | 9/2013 | Averkiou et al. |
| 2005/0033179 | A1* | 2/2005 | Gardner ............... A61B 8/0883 600/458 |
| 2007/0167779 | A1* | 7/2007 | Kim .................... A61B 8/08 600/443 |
| 2008/0221442 | A1* | 9/2008 | Tolkowsky .......... A61B 6/5217 600/425 |
| 2013/0172730 | A1* | 7/2013 | Cohen .................. A61B 6/12 600/424 |
| 2013/0336551 | A1* | 12/2013 | Clingman ............ A61B 5/0095 382/128 |
| 2014/0018708 | A1* | 1/2014 | Dunbar ................ A61N 7/00 601/2 |

OTHER PUBLICATIONS

"A Posteriori Respiratory Gating in Contrast Ultrasound for Assessment of Hepatic Perfusion, . . . " Renault et al , Physics in Medicine and Biology, Bristol, GB vol. 50, No. 19, p. 4465-4480.

"Imaged Based Cardiac Phase Retrieval in Intravascular Ultrasound Sequences" Aura Hernandez-Sabate et al, IEEE Transactions on Ultrasonics, Ferroelectronics, and Frequency Control, vol. 58, No. 1, Jan. 1, 2011 p. 60-72.

"Automatic Phase Determination for Retrospectively Gated Cardiac CT" Manzke et al, Medical Physics, Melville, NY vol. 31, No. 12, Nov. 22, 2004, p. 3345-3362.

* cited by examiner

ELIMINATING MOTION EFFECTS IN MEDICAL IMAGES CAUSED BY PHYSIOLOGICAL FUNCTION

This application is the U.S. National Phase application under 35 U.S.C. §371 of International Application No. PCT/IB2014/058293, filed on Jan. 15, 2014, which claims the benefit of U.S. Provisional Application No. 61/753,898 filed on Jan. 17, 2013. These applications are hereby incorporated by reference herein.

This invention relates to ultrasonic diagnostic imaging systems and, in particular, to the use of ultrasonic diagnostic imaging systems to assess the progress of therapeutic treatment of tumors.

International patent publication WO 2006/090309 (Bruce et al.) describes an ultrasonic imaging technique for detecting lesions in the liver by use of an ultrasonic contrast agent. A bolus of contrast agent is introduced into the body and the time of arrival of the contrast agent in the liver is detected. When a bolus of contrast agent travels through the blood vessels of the body and begins to appear at a specific organ or location in the body, the build-up of contrast in the images is termed the "wash-in" of the contrast agent. As the infusion of contrast agent plateaus at the location in the body and then declines as it is carried away from the location by the flow of blood, the decline is termed the "wash-out" of the contrast agent. In the aforementioned patent publication the inventors take advantage of the fact that the flow of blood to the liver comes from two sources, the hepatic artery and the portal vein. Since the flow of blood during the first, arterial phase of blood flow will perfuse HCC and metastatic liver lesions first, the inventors identify such lesions by detecting the times of arrival of contrast agent in the liver during the arterial and the later portal phase of blood flow. An area of early wash-in of contrast agent to the liver can be symptomatic of a lesion.

Once a lesion or metastasis has been identified by this and/or other means, a treatment regimen is generally prescribed by a physician. The therapy may involve hyper-/hypothermia, cytotoxic chemotherapy, or anti-angiogenesis agents, for example. The therapy is usually not performed in a single session, but in several sessions over a period of weeks or months. At each therapy session it is generally desirable for a physician to assess the progress of the therapy to determine its effectiveness for the patient. The lesion or metastasis may be imaged diagnostically to see whether it is shrinking, for instance. But often the progress of treatment is slow and only small changes in the lesion or metastasis have occurred since the previous session. In such instances it is desirable to assess the progress of therapy quantitatively by measuring certain characteristics of the tumor. One such measure is the regression of tumor angiogenesis. As a lesion or metastasis shrinks with the necrosis of its cells, the microvasculature which developed to nourish the lesion will provide a smaller supply of blood for the lesion and may itself begin to shrink. One quantitative approach is to assess this regression of angiogenesis, the decline in performance of the lesion's microvasculature. A preferred technique for doing this is with a contrast agent which brightly illuminates the blood flow during the uptake of blood containing the agent, and the subsequent decline in brightness during the wash-out phase of the contrast agent. Measurement of the time-intensity curve of this reperfusion enables precise assessment of the success of the treatment therapy toward lesion necrosis. But the acquisition of the necessary image sequence of contrast agent wash-in and wash-out requires that the imaging probe steadily image the lesion in the image plane during the wash-in and wash-out period of the contrast agent, which can last for as long as 100 seconds or more. However, the liver is adjacent to the diaphragm in the body, causing the patient's respiratory motion to cause movement of the anatomy in relation to the image acquisition plane of the probe during the imaging procedure. This movement can cause the lesion to move into and out of the image plane during the procedure. As a result, the brightness of the lesion and its contrast agent in the image will vary with the lesion movement rather that solely due to contrast agent wash-in and wash-out. Consequently it is desirable to eliminate these unwanted motional effects when acquiring images used for perfusion assessment.

One technique for eliminating motional effects is described in U.S. Pat. No. 8,529,453 (Averkiou et al.) This technique involves acquiring images of the target anatomy, in this case the liver, which also show a portion of the diaphragm in the image. The size and position of the diaphragm in the images is used as a landmark. Images containing the diaphragm in the desired size and position are used for perfusion assessment, while images in which the diaphragm has changed its size and/or position or is absent entirely are deleted from subsequent processing. This in effect retains for processing only those images in which the lesion is shown in a consistent image plane. But recognition and deletion of images from the sequence is a manual process, requiring individual inspection and assessment of each image and its view of the diaphragm. Accordingly it is desirable to eliminate motional effects in an automated process which is both robust and requires less intensive user analysis of images.

In accordance with the principles of the present invention, methods are described for processing medical images so that movement due to a certain physiological function, such as the cyclic movement due to respiration or cardiac motion, can be identified and selectively removed from subsequently processed images. This is preferably done by processing only those image frames which belong to the same range of phases of the motion cycle. By processing only those image frames acquired during the same phase range of the motion cycle, the image data is more uniformly affected by the motion and disparate motional effects are largely eliminated from the data, allowing for more precise quantitative assessment of anatomical performance such as perfusion. Clinical applications of the methods include liver, kidney, pancreas, breast, and prostate cancer assessment.

In one implementation, a sequence (loop) of images is acquired during one, and preferably more, cycles of the motion. The normal breathing rate of an adult at rest is 8-16 breaths per minutes, so the acquisition of a one-minute loop will acquire images over about 8-16 cycles of respiratory motion, for instance. The acquired images are tagged with their times of acquisition so that these times can be related to phases of the motion. Strong reflecting structures are identified in the images and their motion followed throughout the loop, which is identified by their cyclic variation in position and/or brightness throughout the loop. For instance, a reflector may start at one location in an image, move to another location over a first series of images, then back to its original location over a second series of images, the time to acquire the two series of images being the time of one cycle of motion. As a second example, a reflector may start with a given brightness in an image, increase in brightness during a first series of images, then decrease in brightness back to its original intensity during a second series of images. Again, the time required to acquire the two series of images is the time of a motion cycle. The identified time or times of motion cycles may be compared with typical cycle times of the physiological function in question to see that they correlate. For example, if an identified motion cycle is outside an expected range of 5-20 breaths per minute, the cycle measurement would be discarded as a respiratory cycle and another cycle measurement made.

Once the motion cycles of the loop have been identified, those images which were acquired during desired phases of the motion cycle are accepted for further processing while the remainder are discarded. For example, it may be desired to accept for processing only those images which were acquired during a 25% range of phases of a respiratory cycle. Images acquired within this range of the respiratory phase of each cycle are then accepted for processing for quantified measurement, such as time-intensity curve and reperfusion measurement.

Figure 1:
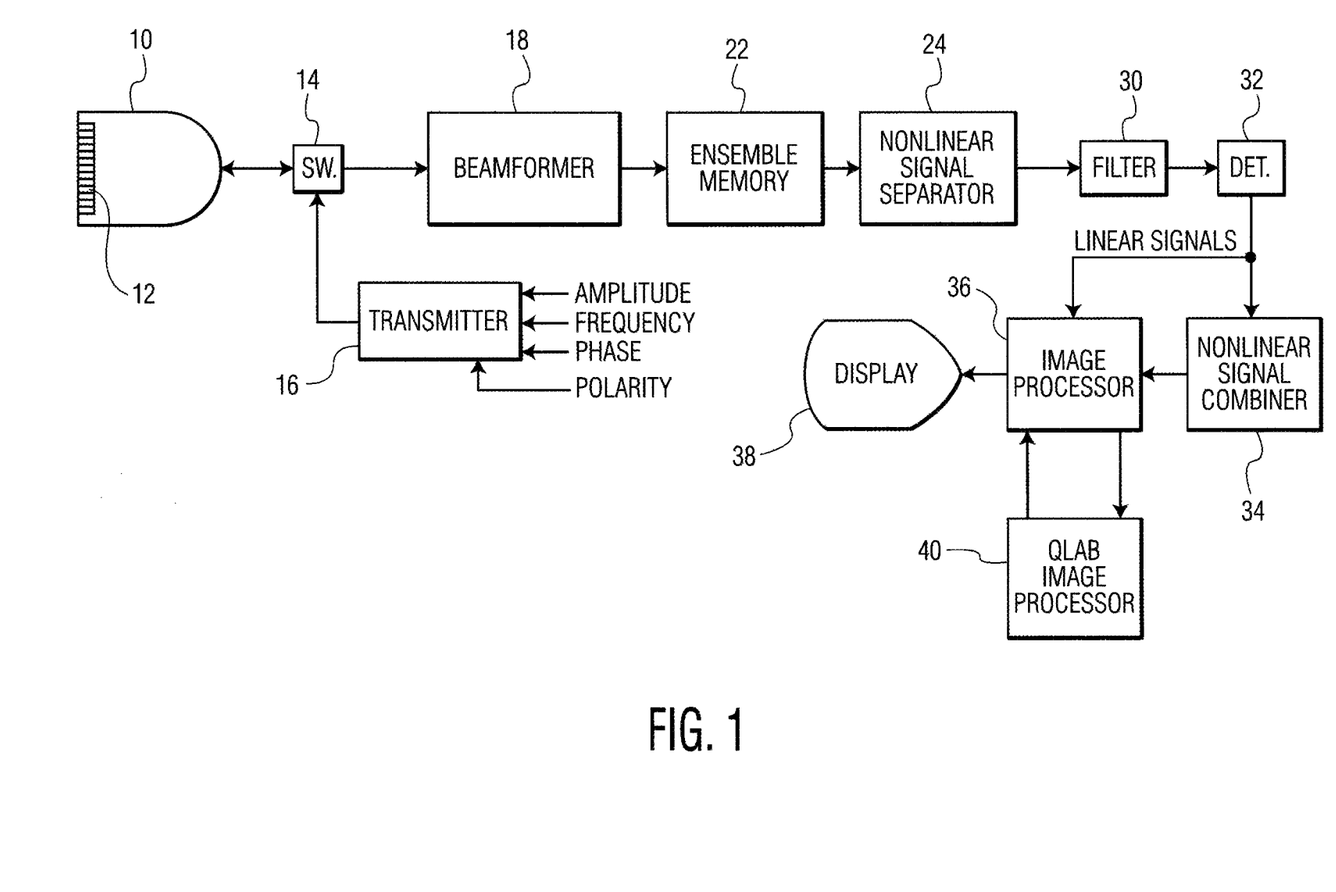
FIG. 1 illustrates in block diagram form an ultrasonic diagnostic imaging system constructed in accordance with the principles of the present invention.

Referring first to FIG. 1, an ultrasound system constructed in accordance with the principles of the present invention is shown in block diagram form. This system operates by scanning a two or three dimensional region of the body being imaged with ultrasonic transmit beams. As each beam is transmitted along its steered path through the body, the beam returns echo signals with linear and nonlinear (fundamental and harmonic frequency) components corresponding to the transmitted frequency components. The transmit signals are modulated by the nonlinear response of contrast agent microbubbles encountered by the beam, thereby generating echo signals with harmonic components.

The ultrasound system of FIG. 1 utilizes a transmitter 16 which transmits waves or pulses of a selected modulation characteristic in a desired beam direction for the return of harmonic echo components from scatterers within the body. The transmitter is responsive to a number of control parameters which determine the characteristics of the transmit beams, including the frequency components of the transmit beam, their relative intensities or amplitudes, and the phase or polarity of the transmit signals. The transmitter is coupled by a transmit/receive switch 14 to the elements of an array transducer 12 of an ultrasound probe 10. The array transducer can be a one dimensional array for planar (two dimensional) imaging or a two dimensional array for two dimensional or volumetric (three dimensional) imaging. A two dimensional matrix array can also be operated in an xMatrix mode in which a single plane (xPlane) which can be steered over a volumetric region is scanned by the matrix array probe.

The transducer array 12 receives echoes from the body containing fundamental (linear) and harmonic (nonlinear) frequency components which are within the transducer passband. These echo signals are coupled by the switch 14 to a beamformer 18 which appropriately delays echo signals from the different transducer elements then combines them to form a sequence of linear and harmonic signals from along the beam direction from shallow to deeper depths. Preferably the beamformer is a digital beamformer operating on digitized echo signals to produce a sequence of discrete coherent digital echo signals from a near field to a far field depth of the image. The beamformer may be a multiline beamformer which produces two or more sequences of echo signals along multiple spatially distinct receive scanlines in response to a single transmit beam, which is particularly useful for 3D imaging. The beamformed echo signals are coupled to an ensemble memory 22.

In the ultrasound system of FIG. 1, multiple waves or pulses are transmitted in each beam direction using different modulation techniques, resulting in the reception of multiple echoes for each scanned point in the image field. The echoes corresponding to a common spatial location are referred to herein as an ensemble of echoes, and are stored in the ensemble memory 22, from which they can be retrieved and processed together. The echoes of an ensemble are combined in various ways by the nonlinear signal separator 24 to produce the desired nonlinear or harmonic signals. For example, two pulses with different phase or polarity modulation can be transmitted to each point in the image field. When the echoes resulting from the two pulses are received by the ultrasound system and additively combined, the different modulation causes the fundamental frequency components of the echoes to cancel and the harmonic components to reinforce each other. This separates out the harmonic components of the echo signals. Alternatively, when the two echoes are subtracted from each other, the fundamental frequency components are reinforced and the harmonic components cancel. This separates out fundamental frequencies for construction of a standard B mode image. This modulation is referred to as "pulse inversion," and can be done by phase, polarity or amplitude modulation as described in U.S. Pat. No. 5,706,819 (Hwang et al.), U.S. Pat. No. 5,951,478 (Hwang et al.), and U.S. Pat. No. 5,577,505 (Brock Fisher et al.)

The separated signals are filtered by a filter 30 to further remove unwanted frequency components, then subjected to B mode or Doppler detection by a detector 32. The detected signals are coupled to a nonlinear signal combiner 34 to reduce image speckle content. The signals are then processed for the formation of two dimensional, three dimensional, spectral, parametric, or other desired image in image processor 36, and the image is then displayed on a display 38. Detected fundamental (linear) signals which do not need speckle reduction processing are coupled directly to the image processor 36 for image formation and display.

In the system of FIG. 1, the ultrasound image data is also coupled to a QLab image processor 40 for the production of time-intensity curves and contrast agent wash-in and wash-out characteristics. The time-intensity curves and characteristics produced by the QLab processor are coupled back to the image processor where they may be displayed numerically or graphically on the display 38 along with the ultrasound images. A standard QLab processor which is suitable for the production of time-intensity curves is available from Philips Healthcare of Andover, Mass.

A standard QLab processor produces the well-known time-intensity curves, also referred to as perfusion curves or reperfusion curves. See U.S. Pat. No. 5,833,613 (Averkiou et al.), international patent publication WO 2005/099579 (Rafter), and international patent publication WO 2005/054898 (Garg et al.) As these publications illustrate, the build-up of contrast agent at points in the tissue (points in the image) is monitored during the arrival of the contrast agent at locations in the body. The amount of contrast agent at a point is indicated by the intensity of echoes returned from contrast agent microbubbles at each point, and is present in a sequence of images acquired by low power (low MI) transmission as the contrast agent washes into the tissue. A time-intensity curve can be formed of this build-up of contrast intensity and its subsequent decline during wash-out of the contrast agent for each point in the tissue which returns the time sequence of echoes frame-by-frame. A qualitative presentation of the time-intensity curves for the entire tissue being viewed can be formed by coloring each pixel in an anatomical image with a color that represents a parameter of the time-intensity curves at each point in the image. The Garg et al. application illustrates the formation of a parametric image of the myocardium where the color of each pixel in the image represents the peak level attained by the time-intensity curve at each point in the myocardium, for example. Alternatively, the slope of the time-intensity curve can be used to indicate the rate of reperfusion instead of the peak. See also U.S. Pat. No. 6,692,438 (Skyba et al.)

In an implementation of the present invention, contrast agent perfusion echo data is acquired over a sequence (loop) of images as the contrast agent arrives at the location of a metastasis in the body, builds up, and then washes out. The intensity values of the echoes will thus start from a baseline level of no contrast agent present, then rise, plateau, and decline as the contrast agent washes out. A curve-fitting algorithm then fits this data variation to an error function defined as $$I(t) = A[erf\{(t-t_0)/T\} + I_0]$$

where I(t) is the linear intensity at time t, A is the maximum intensity over the baseline offset, T is wash-in time parameter which is linearly proportional to wash-in time (e.g., from 5%-95%), $I_0$ is baseline offset, and $t_0$ is a time offset. The wash-in time is preferably extracted from the fitted curve rather than the noisy image data. Preferably the contrast agent echo data does not undergo data compression prior to this processing so that the data remains in its acquired linear relationship. Another approach is to fit the whole time-intensity curve (instead of just the wash-in part) to appropriate mathematical models as the lognormal distribution for example defined as $$I(t) = \frac{A}{\sqrt{2\pi}\,\sigma(t-t_0)} e^{\frac{[\ln(t-t_0)-\mu]^2}{2\sigma^2}} + C$$

where $\mu$ and $\sigma$ are the mean and standard deviation of the normal distribution from which the logarithmic transformation was obtained. The curve can be scaled horizontally by varying $\mu$ and changed in terms of skewness by varying $\sigma$. The area under the curve is A, $t_0$ is the time offset, and C is the baseline intensity offset. The lognormal fitted curve is used to extract the wash-in time.

Figure 2:
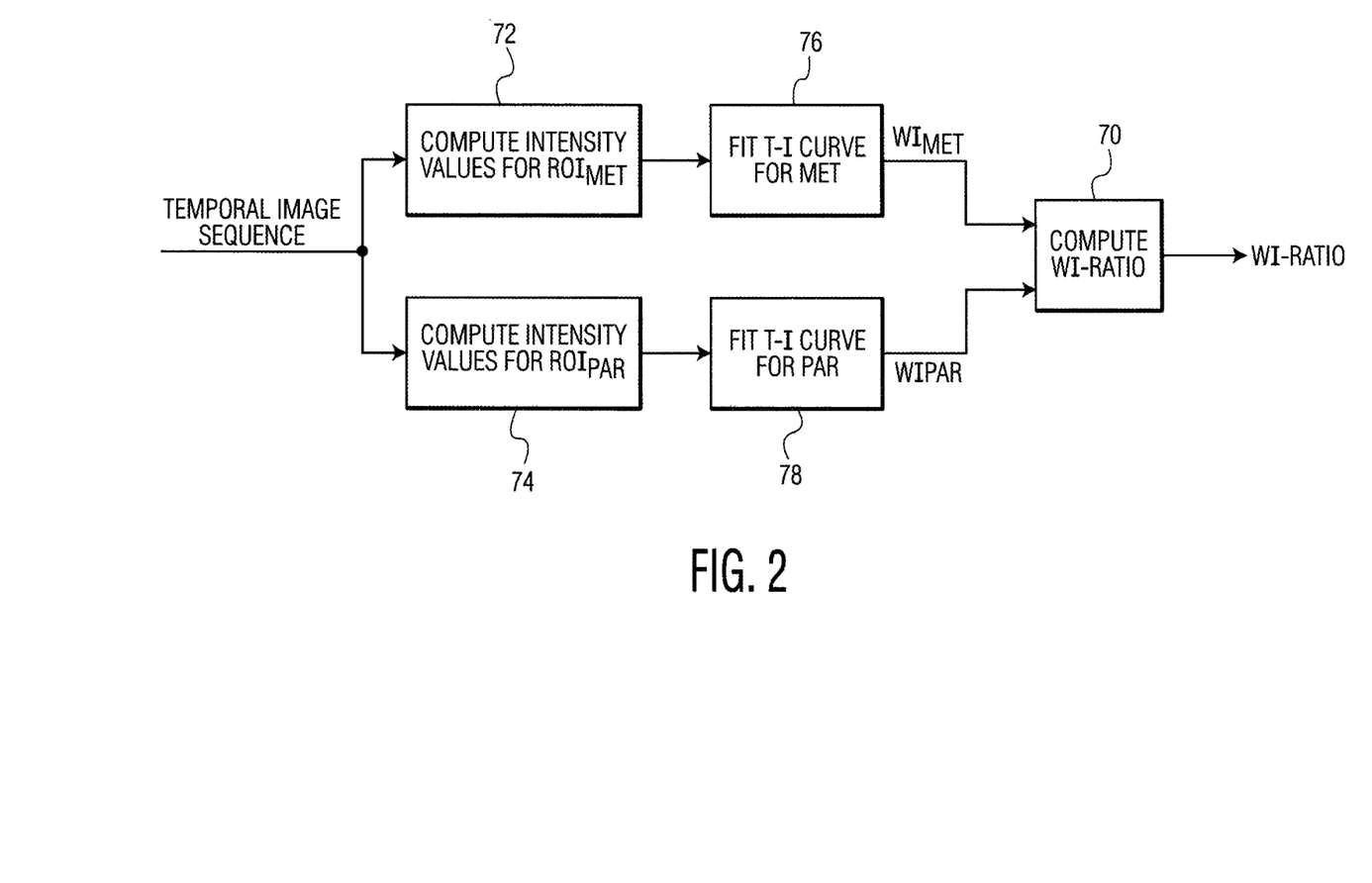
FIGS. 2 and 3 illustrate details of the operation of the QLab processor of FIG. 1 when calculating a time-intensity curve for perfusion assessment.

The ultrasound system of FIG. 1 can compute a quantitative measure of the perfusion of a metastasis, a parameter referred to as the wash-in time ratio (WITR). The WITR is computed as shown by the block diagram of FIG. 2. From a temporal sequence of images of a metastasis or lesion during contrast agent wash-in and wash-out, contrast agent intensity values are computed for the $ROI_{Met}$ of the metastasis, a region of interest in the metastasis, as indicated by box 72. As explained above, these values can be computed by combining the pixel values of the metastasis ROI for each image of the sequence acquired during wash-in. In box 74 intensity values are computed for an $ROI_{Par}$ of normal parenchyma of the tissue. This may be done by tracing a region of normal tissue in an image of the liver metastasis and using the normal tissue perfusion pixel values within this second tracing. These values are therefore perfusion values of normal tissue. In box 76 a time-intensity curve is fitted to the perfusion values of $ROI_{MET}$, and in box 78 a time-intensity curve is fitted to the perfusion values of $ROI_{PAR}$. The fit is not always necessary but it gives a better estimation of the various hemodynamic parameters that may be extracted from time-intensity curves. While these parameters can be measured directly from the data, noise in the data can interfere with the accuracy of the measurement, hence the preference for curve-fitting. A wash-in time parameter WIT is found for each curve, for example by use of the error function or lognormal distribution described above. This determines a wash-in time parameter for both the metastasis and normal parenchyma, $WIT_{MET}$ and $WIT_{PAR}$, respectively. A wash-in time ratio WITR is then computed from the two wash-in parameters by dividing $WIT_{Met}$ by $WIT_{Par}$ as shown by box 70. The effect of normalizing $WIT_{Met}$ by the wash-in time parameter of normal tissue is to reduce or eliminate the effects of variables in the procedure such as bolus size, cardiac output, and ultrasound system settings, which may differ from one therapy session to another. Thus, comparable quantitative measures of the growth or shrinkage of the metastasis as indicated by its angiogenesis can be produced for each therapy session over the period of weeks or months that the patient is being treated.

Figure 3:
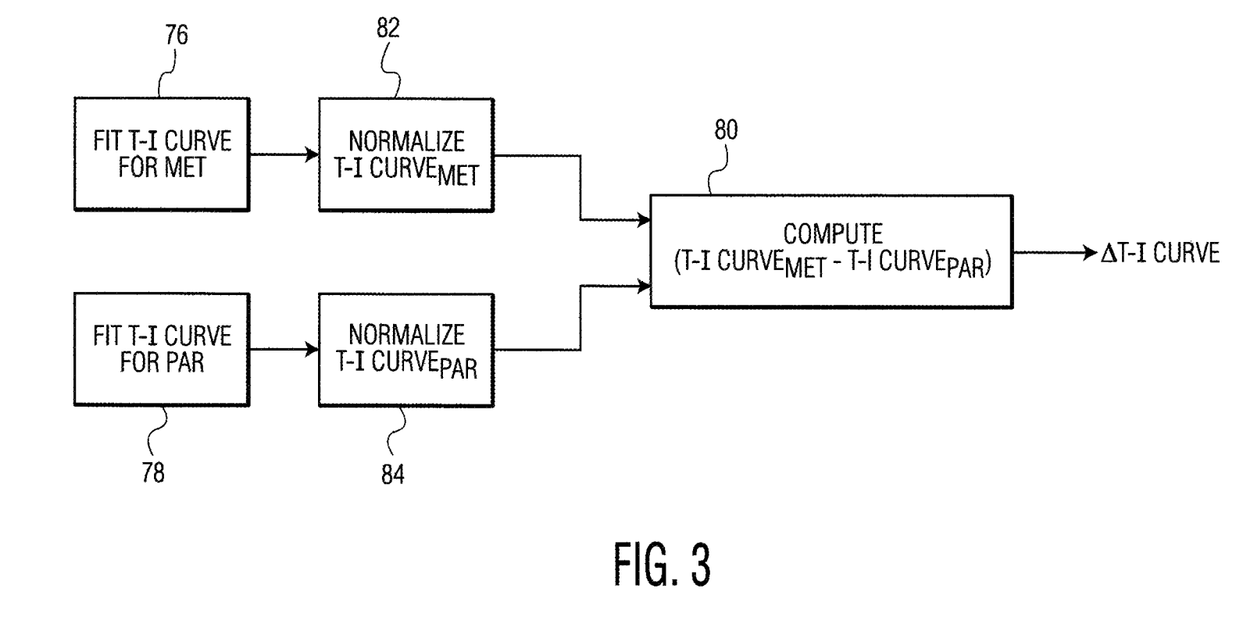

Another quantified measure of metastasis angiogenesis which reduces or removes the effects of bolus injection rate, cardiac output of the patient, or variation in machine settings is illustrated in FIG. 3. A time-intensity curve is fitted for each of the ROIs of the metastasis and the parenchyma as shown in boxes 76 and 78. In boxes 82 and 84, the range of each time-intensity curve is normalized. A convenient normalization scale is zero to one. In box 80 a difference curve $\Delta T$–I Curve is computed as the difference between the two normalized curves T–I Curve$_{MET}$ and T–I Curve$_{PAR}$. Further details of this production of a time-intensity curve may be found in U.S. Pat. No. 8,529,453 (Averkiou et al.) which is incorporated herein by reference.

Figure 4:
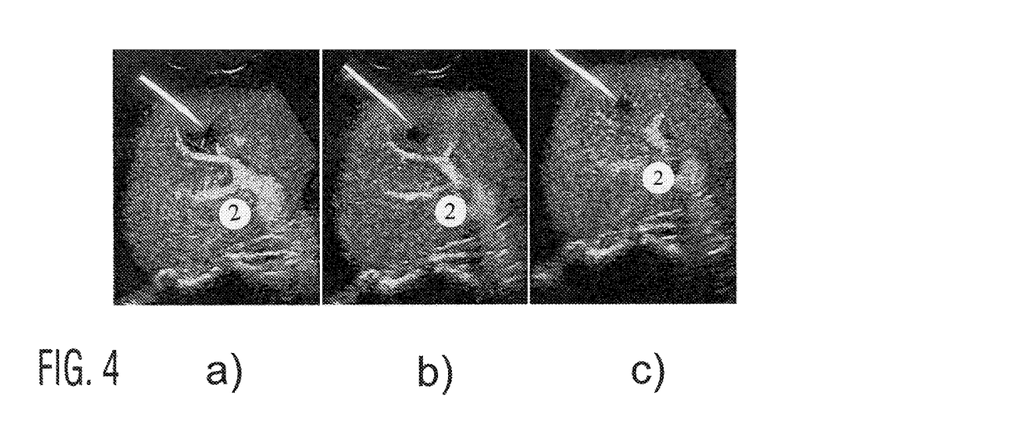
FIGS. 4*a*, 4*b*, and 4*c* illustrate the variation of the appearance of a tumor and blood vessels as the image plane moves due to respiratory motion.

As mentioned above, a typical period of contrast agent wash-in and wash-out can last for as long as 100 seconds or more. This means that a clinician acquiring the image data must maintain the same image of the lesion steadily for 100 seconds so that each intensity value is of the same region of the lesion. If the probe moves during the acquisition, for instance, the lesion can move out of the image plane and the data acquired cannot be used. Even if the probe is held steady against the body of the patient, the lesion can still move relative to the probe field of view due to the respiratory motion of the patient. This is illustrated by the ultrasound images of FIGS. 4a, 4b, and 4c. These are images of a liver lesion indicated by the white pointer over the images with the main vessels (portal vein and hepatic artery) visible in the images beneath the lesion and above the circle 2. These images were acquired while the sonographer was trying to hold the probe steady against the abdomen of the patient so that the same anatomy was continuously shown in the images from one image to the next. But the images are affected by the breathing of the patient and the respiratory motion causes the lesion and the desired image to move in and out of the image plane of the probe. This is best illustrated in these images by the variation seen of the hepatic artery. In FIG. 4a it is seen that the image cut plane through the portal vein is through the central region of the vessel and it appears large in the image. But that central portion of the vessel has moved out of the image plane in FIG. 4b and it appears much thinner as a different cut plane through the vein has moved into the image plane. In FIG. 4c the vessel is barely visible as it has move almost completely out of the probe's image plane. Corresponding, the size and position of the lesion indicated by the white pointer also changes from one image to another. One way to overcome the adverse effect of respiratory motion is to gate the image acquisition to the respiratory cycle. A respiratory signal can be acquired by known means such as an elastic band with strain or pressure sensors around the chest of the patient. Another technique is to transmit small signals between sensors across the chest of the patient and measure the patient's chest impedance variations. These and other techniques can produce cyclical signals of the respiratory cycle and can be used to gate the acquisition of images to the same phase of the respiratory cycle.

Figure 5:
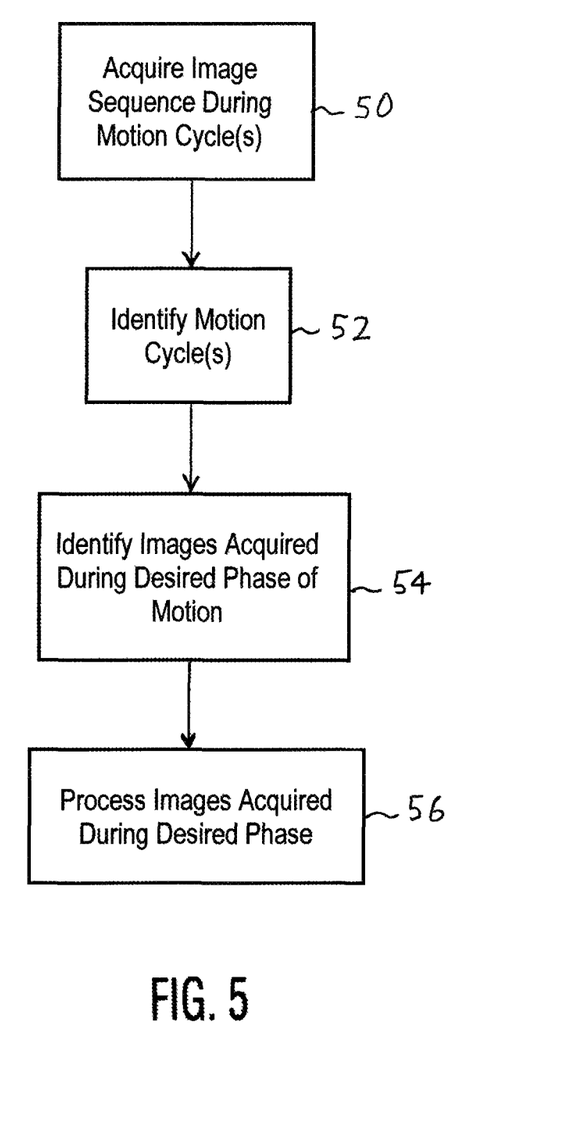
FIG. 5 illustrates in block diagram form a first method for removing respiratory motion effects from image characteristic quantification as performed by the ultrasound system of FIG. 1 in accordance with the principles of the present invention.

In accordance with the principles of the present invention, respiratory gating is performed by image post-processing as shown by the block diagram of FIG. 5, which illustrates one implementation of the present invention. In step 50 a sequence of successive images is acquired during one or more motion cycles. This image loop could be a sequence of images acquired during the 100+ seconds of contrast agent wash-in and wash-out mentioned above, and could comprise hundreds or even thousands of images. Obviously, manually processing this many images would be a painstaking and likely inaccurate task. An image loop this long would cover over 20 respiratory cycles at a nominal breathing rate of thirteen breaths per minute. A loop this long would cover about 100 heartbeat cycles at a nominal heart rate of one beat per second. This loop would therefore be contaminated by many cycles of motion of either physiological phenomenon.

In step 52 the cyclical motion is identified. One way to do this may be understood with reference to the images of FIG. 4. It is seen in these images that the main hepatic vessels above the circle 2, filled as it is with contrast agent, is a very bright reflector in the images, indeed it is the largest bright structure in the images. The vein is seen to be at its largest and brightest when the cut plane of the image passes through the center of the artery as it is in FIG. 4a, and less so in the other images. Thresholding or decimation of the pixel values of these images below the hepatic artery brightness will extract the pixels of the hepatic artery from the center of the images and the pixel values summed or integrated to indicate the brightness of this structure in each image. The recurrence of the peak brightness of the portal vein each time it moves fully into the cut plane of the probe image plane indicates the periodicity of the respiratory motion moving the image plane, and the duration of the motional cycle is the time between the acquisition of two such images as shown by their time-tagging. With the motion cycle thus identified, the images acquired during a desired phase or phase range of the motion are identified in step 54. For instance, it may be decided to use each image of peak brightness (FIG. 4a) and the five images preceding and succeeding the peak brightness image in every respiratory cycle. These eleven images of each respiratory cycle are then selected for perfusion assessment processing as shown in step 56. The images which were acquired during less desirable phases of the respiratory cycle are omitted from processing. As a result the perfusion measurement should be relatively unaffected by the effects of respiratory motion.

Figure 6:
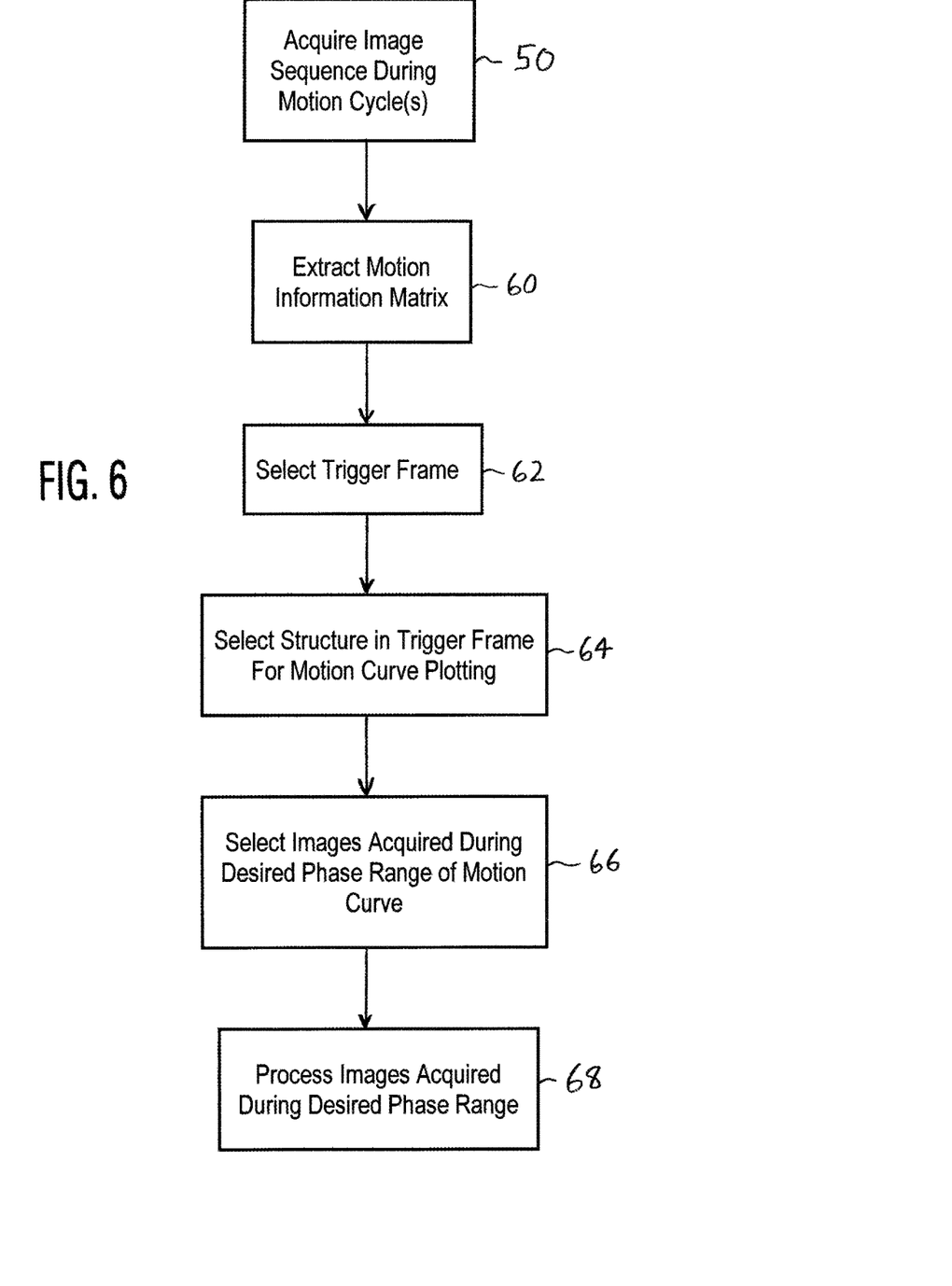
FIG. 6 illustrates in block diagram form a second method for removing respiratory motion effects from image characteristic quantification as performed by the ultrasound system of FIG. 1 in accordance with the principles of the present invention.
Figure 7:
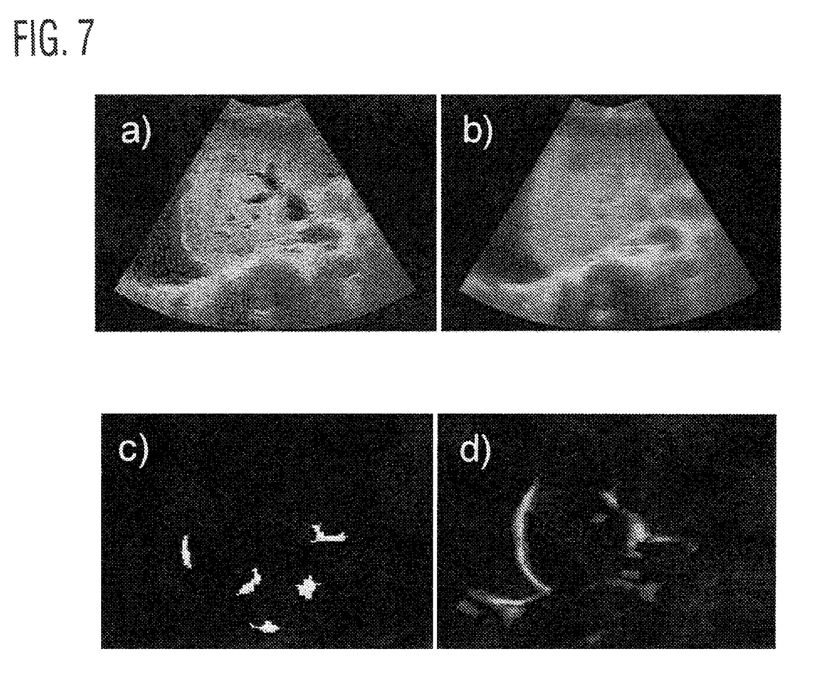
FIGS. 7*a*, 7*b* and 7*c* and 7*d* are ultrasound images illustrating the formation of a motion information matrix used to extract a respiratory curve in accordance with the present invention.

FIG. 6 illustrates a preferred implementation of the present invention in block diagram form. Using the acquired image sequence from step 50 in this drawing, the motion information contained in the image sequence is extracted in what is referred to herein as a "motion information matrix." FIGS. 7a-7d illustrate one way to form a motion information matrix (MIM). FIG. 7a illustrates an ultrasound image of the liver and FIG. 7b illustrates an image which is an average of all of the image frames in the loop containing the image of FIG. 7a. Each frame of the loop such as that of FIG. 7a is subtracted from the average of the frames (FIG. 7b) and pixel intensities above a certain threshold are assigned a value of 1 with all others assigned a value of zero. This produces a binary image of bright structures in each image such as the one shown in FIG. 7c. The resulting binary images are added together to form an MIM as shown in FIG. 7d, an image of structures which can be readily identified in the image loop and which are potentially affected by motion.

The next step 62 is the selection of a trigger frame from the loop. A trigger frame is one which will be included among the finally processed images. It may be one, for instance, in which the lesion is clearly defined as by a high intensity or large size in the image. Or it may be an image which appears virtually identical to previously and/or successively acquired images in the loop and thus exhibits little or no motion contamination. The trigger frame may be designated by the user by inspection, or may be selected by an automated method such as by subtracting each pair of successive frames and using using one of the frames which produced the most minimal difference image. Candidate structures for motion identification are then extracted from the trigger frame for motion curve formation as shown by step 64. This extraction may comprise a binary image produced from the trigger frame as discussed above. The structures extracted from the trigger image are compared with the structures of the MIM to choose one which is significantly affected by motion. A structure of the MIM which varies over a wide intensity range or positional range could be selected, for instance. The frequency of the variation can be compared with the frequency of the physiological phenomenon to ascertain that its variation corresponds to that of the physiological function. If it does not, the structure is disregarded and another structure of the MIM selected for motion identification. To aid in the selection, the structures of the MIM can be ranked in accordance with their likelihood of exhibiting effects of motion. The structure which is found to be the region of greatest interest for motion extraction is then used as a binary mask that is used to extract a curve of the respiratory or other bodily motion. The mask of the structure is applied to the corresponding location in each image in the loop and a series of mean intensity values within the mask extracted from the image frames which exhibit intensity variation during the loop that is representative of the cyclical motion. These mean intensity values are plotted as a function of time (or, equivalently, frame number in the sequence) to yield an approximate respiratory curve. The initial plot may be fitted to an average curve to produce a smoothly varying respiratory curve as shown by respiratory curve 100 in FIG. 8. Known curve fitting techniques may be used to produce a smoothly varying curve, such as a piecewise cubic Hermite interpolating polynomial fitted to the peaks and troughs of the approximate curve, for instance.

Figure 8:
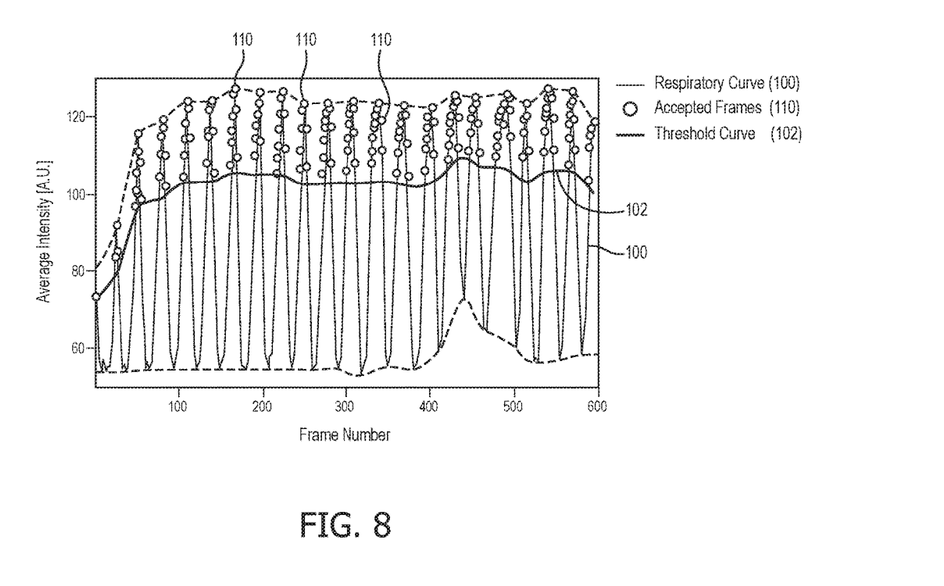
FIG. 8 illustrates respiratory gating using a respiratory curve in accordance with the present invention.

FIG. 8 illustrates a respiratory curve 100 formed from respiratory motion mean intensity variation of a structure over a loop of 600 image frames. It is seen that the curve 100 indicates 21 respiratory cycles occurring during acquisition of the 600 image frames. The small circles 110 at the top of the plot indicate some of the discrete frames of the loop. The circles are shown on the respiratory curve in correspondence to the points in the respiratory cycles. A threshold 102 is applied to the curve 100 to delineate the phase range of each respiratory cycle during which image frames will be accepted for perfusion processing. For instance, suppose that the lower peaks of the respiratory curve are points where the patient has fully inhaled, and the upper peaks of the curve are points where the patient has fully exhaled. The clinician may decide to use image frames that all were acquired around the time of full exhalation, for example, just before and just after the patient has fully exhaled. The system then applies a threshold 102 as shown in the drawing which delineates, in this example, this phase range of each respiratory cycle, which is seen in this example to comprise about 30% of each cycle. The image frames acquired during this respiratory phase range, the frames represented by the circles 110, are then selected for processing as shown in step 66 of FIG. 6. The processed image frames of step 68 are thus a set of frames which all were acquired during the same phase range of respiratory motion and should thus generally correspond spatially to each other, with the structures and lesions of the images appearing generally the same in size and position in each of the processed images. This will yield accurate quantification of physiological measures and functions such as time-intensity curve production and perfusion assessment. The data for such quantification may be selected from the accepted images using the trigger frame. The lesion is identified in the trigger frame as a region of interest (ROI), and data extracted from the location of the ROI in each of the accepted image frames. This data is then processed to produce time-intensity curves as described above and in European patent EP 2 234 544 B1, the contents of which are incorporated herein.

Figure 9:
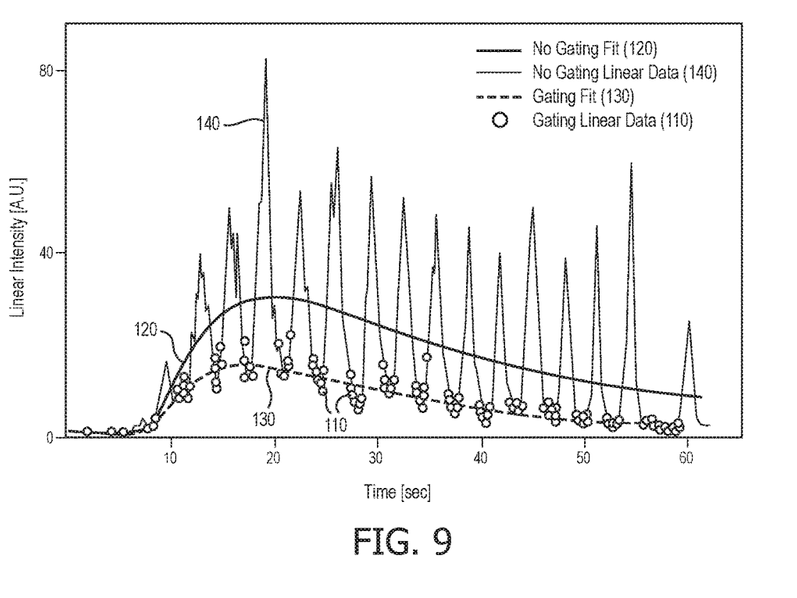
FIG. 9 illustrates time-intensity curves of a liver metastasis processed with and without respiratory gating in accordance with the present invention.

The foregoing technique was applied to clinically acquired image loops from a number of liver cancer patients. FIG. 9 illustrates time-intensity curves produced in one of these cases, both with and without respiratory phase gating. The intensity data of a region of interest in the images was fitted to a lognormal function to produce time-intensity curves of reperfusion. The goodness of fit was quantified using the R-squared value and the root mean squared error value. The time-intensity curve 120 was produced from data of all of the image frames without gating, and is seen to be affected by the highly oscillatory characteristic of the intensity values 140 sampled at the ROI of the images, which contains large spikes due to sampling of images outside the lesion caused by respiratory motion of the anatomy. When gating is applied in accordance with the present invention only the image frames 110 acquired around the lower phase range of motion are used. The oscillatory effects of the intensity data are greatly diminished because sampling more uniformly occurs within the lesion since the size and position of the lesion ROI are more uniform over the image frames 110 accepted for processing.

The mathematical formulae used in an implementation of the present invention is detailed in Appendix A, and their use in a method of the present invention explained.

APPENDIX A

| Step Index | Description | Mathematical Formulae and Description |
|---|---|---|
| 1 | Import the video | $I_{ori} = i(x, y, z)$<br>x is the frame's rows<br>y is the frame's columns<br>z is the number of frames |
| 2 | Decimate the video's frames by 2 for faster processing | $I_{ori} = i(x, y, \hat{z})$<br>$\hat{z} = \left\{ 2n + 1 : n \text{ is an integer, and } 0 \leq n \leq \left\lfloor \frac{(z-1)}{z} \right\rfloor \right\}$ |
| 3 | Compress the video frames for faster processing | $I_{comp} = i(\hat{x}, \hat{y}, \hat{z})$<br>Pixel intensity values corresponding to $\hat{x}, \hat{y}$ pixel coordinates calculated via piecewise constant interpolation (nearest-neighbour interpolation) |
| 4 | Calculated average frame from the compressed video $I_{comp}$ | $I_{ave} = \frac{\sum_{i=1}^{\max(\hat{z})} I_{comp}(\hat{x}, \hat{y}, i)}{\max(\hat{z})}$ |
| 5 | Subtract each frame for the average | $I_{mov} = I_{comp}(\hat{x}, \hat{y}, \hat{z}) - I_{ave}(\hat{x}, \hat{y}) \; \forall \; z$ |
| 6 | Set pixel intensities below a certain threshold to zero in $I_{mov}$ and pixels above that threshold to 1 | $I_{zero}(I_{mov} \leq \text{threshold}) = 0$<br>$I_{thre}(I_{zero} \neq 0) = 1$ |
| 7 | Remove pixels from frames that are surrounded by zeros | $I_{clean} = (I_{thre} \not\supset \text{non zero Intensity pixels surrounded by zero values})$ |
| 8 | Extract $n^{th}$ largest group of connected pixels from each frame | $I_{larg} = (I_{clean} \supset n^{th} \text{ largest group of connected pixels})$ |

APPENDIX A-continued

| Step Index | Description | Mathematical Formulae and Description |
|---|---|---|
| 9 | Perform the morphological operation of close on each frame of $I_{larg}$ with a 4-pixel wide square structuring element | $I_{cloze} = (I_{larg} \otimes S) \ominus S$<br><br>$S = \begin{matrix} 1 & 1 & 1 & 1 \\ 1 & 1 & 1 & 1 \\ 1 & 1 & 1 & 1 \\ 1 & 1 & 1 & 1 \end{matrix}$ |
| 10 | Add all frames of $I_{close}$ together | $I_{sum} = \Sigma_{i=1}^{max(\hat{z})} I_{close}(\hat{x}, \hat{y}, i)$ |
| 11 | Resize the $I_{sum}$ frames to the original resolution of $I_{ori}$ using bicubic interpolation to acquire the MIM | $MIM = resize(I_{sum})$ |
| 12 | Produce average frame of the original video | $I_{ave\_ori} = \dfrac{\Sigma_{i=1}^{max(z)} I_{ori}(x, y, i)}{max(z)}$ |
| 13 | Subtract the T-frame chosen by the user from the $I_{ave\_ori}$ | $I_{mov\_ori} = I_{ori}(x, y, z_{trigger}) - I_{avg\_ori}$ |
| 14 | Repeat steps 6-7 on $I_{mov\_ori}$ | $I_{mov\_ori} \to I_{clean\_ori}$ |
| 15 | Extract the $k^{th}$ largest groups of connected pixels from $I_{clean\_ori}$ | $I_{larg_{ori}} = (I_{clean_{ori}} \supset k^{th}$ largest groups of connected pixels |
| 16 | Perform the morpological operation of close on each frame of $I_{larg\_ori}$ with a 4-pixel wide square structuring element | $I_{close\_ori} = (I_{larg\_ori} \otimes S) \ominus S$<br><br>$S = \begin{matrix} 1 & 1 & 1 & 1 \\ 1 & 1 & 1 & 1 \\ 1 & 1 & 1 & 1 \\ 1 & 1 & 1 & 1 \end{matrix}$ |
| 17 | Extract the x, y coordinates of the contour of each structure in $I_{close\_ori}$ and pass them through a median filter | $x_{filt}[i] = median(x[i], (i) \in w)$<br>$y_{filt}[j] = median(y[j], (j) \in w)$<br>w is the median filter window size |
| 18 | Reconstruct the C-ROIs from the $x_{filt}$ and $y_{filt}$ vectors and store them in $I_{C\text{-}ROI}$ | $x_{filt}, y_{filt} \to I_{C\text{-}ROI}$ |
| 19 | Acquire the total pixel intensity contained in a M × M pixel square with its centre around the centre of gravity of each C-ROI in $I_{C\text{-}ROI}$, across the z-dimenstion (i.e. across the frames) of $I_{ori}(x, y, z)$. | $V^q(i) = I_{ori}(x_{square}, y_{square}, i)$<br>$x_{square}, y_{square}$ are the coordinates assigned to the M × M square around the centre of gravity of each C – ROI<br>i: frame index<br>q: C – ROI index |
| 20 | Smooth the data contained in V(i) using robust locally weighted scatterplot smoothing (RLOESS) and a $2^{nd}$ degree polynormial model | $V^q(i) \to V^q(i)_{smooth}$ |
| 21 | Perform a Fast Fourier Transform (FFT) on each V(i) and retrieve the maximum frequency ($F_{major}$) contained in each V(i) | $P^q(k) = \Sigma_{i=1}^{N} V^q(i)_{smooth} \, w_N^{(j-1)(k-1)}$<br>$P^q_{major} = max|(P^q(k)|$ |
| 22 | Compare the $F_{major}$ of each structure and check if it lies within the reange of the motion the user desires to remove. Remove structures from $I_{C\text{-}ROI}$ that do not fulfil criterion. | $I_{C\text{-}ROI} \to I_{freq\_filt}$ |
| 23 | Element-by-element multiplication of the MIM matrix with $I_{freq\_filt}$ | $I_{intersect} = MIM \odot I_{freq\_filt}$ |
| 24 | Calculate mean value of the matrix elements contained within each ROI in $I_{intersect}$ | $M(i) = \dfrac{\Sigma I_{intersect}(i)}{N(i)}$<br>i: identifies each ROI<br>N(i): number of pixels with each ROI<br>$\Sigma I_{intersect}(i)$: sum of the matrix elements contained in each ROI(i) of $I_{intersect}$ |
| 25 | Choose the ROI with the highest M(i) and store the resulting ROI as a binary image in $I_{E\text{-}ROI}$ | $I_{E\text{-}ROI}$ |
| 26 | Extract the mean intensity contained in $I_{E\text{-}ROI}$, across the frames of the original video. The resulting vector is stored as an IC. | $I_{ROI-intersect} = I_{ori}(x, y, z) \odot I_{E\text{-}ROI}(x, y) \, \forall \, z$<br><br>$IC(z) = \dfrac{\Sigma I_{ROI-intersect}(\acute{x}, \acute{y}, z)}{N} \forall z$<br><br>$\acute{x}, \acute{y}$: row and column coordinates of the intersection between $I_{ori}$ and $I_{E\text{-}ROI}$<br>N: number of pixels of the E – ROI |

APPENDIX A-continued

| Step Index | Description | Mathematical Formulae and Description |
|---|---|---|
| 27 | Gate the IC by finding the peaks and troughs of the IC and keep the frames that are within a user-defined percentage of the peaks, troughs or any other portion of the IC in-between | $I_{ori}(x, y, z) \rightarrow I^i_{gated}(x, y, \hat{z})$<br>$\hat{z}$: Index of frames kept after gating<br>$i$: Index of cyclic motion phase |

What is claimed is:

1. A method for reducing the effect of physiological motion in image data acquired from a sequence of medical images of a subject comprising:
 acquiring a sequence of medical images containing image data of a target region of a subject during the occurrence of cyclical physiological motion affecting the target region;
 using image data in a region of at least some of the images in the sequence to identify cycles of the physiological motion;
 identifying images acquired during a certain range of phases of the identified motion cycles; and
 processing image data of the identified images to assess a property of the target region, wherein using image data further comprises extracting a motion information matrix from the image data, the motion information matrix comprising a combination of at least two thresholded images from the sequence thereby identifying a structure affected by the motion.

2. The method of claim 1, wherein the acquiring step further comprises acquiring a loop of medical images which are affected by respiratory motion or cardiac motion.

3. The method of claim 1, wherein using image data further comprises using image data of the same corresponding location in each of the images to identify cycles of the physiological motion.

4. The method of claim 3, wherein using image data further comprises using intensity image data.

5. The method of claim 1, wherein processing further comprises processing image data of the target region from each of the identified images.

6. The method of claim 1, wherein acquiring further comprises acquiring a sequence of two dimensional medical images of an image plane during the occurrence of physiological motion affecting the target region by moving the target region in and out of the image plane.

7. The method of claim 1, wherein acquiring further comprises acquiring a sequence of two dimensional medical images of an image plane during the occurrence of physiological motion affecting the target region by varying its intensity or location in an image during the acquisition.

8. The method of claim 1, wherein using image data further comprises selecting a trigger frame acquired during the range of phases of one of the cycles, the trigger frame comprising candidate structures that are extracted from the image and used to identify the cycles of the physiological motion.

9. The method of claim 8, wherein using image data further comprises using image data of the trigger frame and data of a motion information matrix along with the frequency of cycles of motion of structures of the trigger frame to select a structure in the images whose image data is to be used for motion curve identification.

10. The method of claim 9, wherein using image data further comprises identifying a motion curve using the variation in brightness or position of the selected structure over the sequence of images.

11. The method of claim 1, wherein using image data of the images to identify cycles of motion further comprises comparing the frequency of cycles of motion to an expected range of frequencies of a cyclical physiological phenomenon.

12. The method of claim 1, wherein processing image data further comprises processing image data from the target region in identified images to produce a time-intensity curve of perfusion.

13. The method of claim 12, wherein processing image data further comprises processing contrast agent image data from an image region containing a tumor or lesion in identified images to produce a time-intensity curve of contrast reperfusion.

14. A method for reducing the effect of respiratory motion in image data of a time sequence of ultrasound images which is to be used to produce a time-intensity curve comprising:
 acquiring a sequence of ultrasound images containing image data of a target region for which a time-intensity curve is to be produced, the sequence being acquired during the occurrence of respiratory motion affecting the target region;
 using image data among at least some of the images in the sequence to identify cycles of the respiratory motion;
 selecting a range of phases of the identified respiratory motion cycles; and
 processing image data of images of the sequence which were acquired at one of the phases of the selected range of phases of the respiratory motion cycles, wherein using image data further comprises extracting a motion information matrix from the image data, the motion information matrix comprising a combination of at least two thresholded images from the sequence thereby identifying a structure affected by the motion.

* * * * *